(12) United States Patent
Volkov

(10) Patent No.: US 7,037,726 B2
(45) Date of Patent: May 2, 2006

(54) METHODS FOR FORMING RECOMBINED NUCLEIC ACIDS

(75) Inventor: Alexander Volkov, Sunnyvale, CA (US)

(73) Assignee: Genencor International, Inc., Palo Alto, CA (US)

( * ) Notice: Subject to any disclaimer, the term of this patent is extended or adjusted under 35 U.S.C. 154(b) by 604 days.

(21) Appl. No.: 10/345,505

(22) Filed: Jan. 16, 2003

(65) Prior Publication Data

US 2003/0129647 A1 Jul. 10, 2003

Related U.S. Application Data

(62) Division of application No. 09/566,645, filed on May 8, 2000, now Pat. No. 6,534,292.

(51) Int. Cl.
*C12P 19/34* (2006.01)

(52) U.S. Cl. .................. 436/501; 435/6; 435/91.1; 435/91.2

(58) Field of Classification Search ............ None
See application file for complete search history.

(56) References Cited

U.S. PATENT DOCUMENTS

| 5,093,257 A | 3/1992 | Gray |
| 5,270,170 A | 12/1993 | Schatz et al. |
| 5,521,077 A | 5/1996 | Khosla et al. |
| 5,830,696 A | 11/1998 | Short |

FOREIGN PATENT DOCUMENTS

| EP | 0 408 295 A | 1/1991 |
| EP | 0 563 103 B1 | 12/1991 |
| FR | 2 782 323 A | 2/2000 |
| WO | WO 87/01374 | 3/1987 |
| WO | WO 94/12632 | 6/1994 |
| WO | WO 95/22625 | 8/1995 |
| WO | WO 97/07205 | 2/1997 |
| WO | WO 97/15657 | 5/1997 |
| WO | WO 97/46670 | 12/1997 |
| WO | WO 98/01581 | 1/1998 |
| WO | WO 98/05765 | 2/1998 |
| WO | WO 98/10102 | 3/1998 |
| WO | WO 98/17684 | 4/1998 |
| WO | WO 98/28416 | 7/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/42867 | 10/1998 |
| WO | WO 98/51802 | 11/1998 |

OTHER PUBLICATIONS

Aslanidis et al., Ligation-independent cloning of PCR products (LIC-PCR), *Nucleic Acids Research*, V. 18, No. 20 pp. 6069-6074 (1990).

Bashkirov, V., et al., "Interplasmidic illegitimate recombination in *Bacillus subtilis,*" *Mol Gen Genet*, V. 1, 213 pp. 465-470 (1988).

Beck et al., "Introduction of arbitrary sequences into genes by use of class IIs restriction enzymes," *Nucleic Acids Research*, V. 22, N. 5, pp. 886-887 (1994).

Berger, S. et al, "Phoenix Mutagenesis: One-Step Reassembly of Multiply Cleaved Plasmids with Mixtures of Mutant and Wild-Type Fragments," *Analytical Biochemistry*, 214, pp. 571-579 (1993).

Bron, S. et al, "Ultraviolet Inactivation and Excision-Repair in *Bacillus subtilis,*" *Mutation Research*, 15 pp. 1-10 (1972).

Canosi, U. et al, "Plasmid Transformation in *Bacillus subtilis*: Effects of Insertion of *Bacillus subtilis* DNA into Plasmid pC194," *Mol Gen Genet*, 181, pp. 434-440 (1981).

Cheng, S. et al, "Effective amplification of long targets from cloned inserts and human geonomic DNA," *Proc. Natl. Acad. Sci. USA*, V.91, pp. 5695-5699 (1994).

Contente, S. et al, "Marker Rescue Transformation by Linear Plasmid DNA in *Bacillus subtilis,*" *Plasmid*, 2, pp. 555-571 (1979).

Crameri, A. et al, "DNA shuffling of a family of genes from diverse species accelerates directed evolution," *Nature*, V. 391 pp. 288-291 (1998).

Crameri et al., "Combinatorial Multiple Cassette Mutagenesis Creates All the Permutations of Mutant and Wild-Type Sequences," *Benchmarks*, V. 18, No. 2, pp. 194-196 (1995).

(Continued)

*Primary Examiner*—Juliet C. Switzer
(74) *Attorney, Agent, or Firm*—Genecor International, Inc.

(57) ABSTRACT

Described herein are methods for generating recombined nucleic acids. In one method, fragments of a sequence are provided wherein the fragments have non-extendable 3' ends. A primer is provided and the primer and fragments are reacted under conditions to extend the primer to form a recombined nucleic acid molecule. In the methods herein, the non-extendable fragments act only as templates, rather than as templates and primers.

4 Claims, No Drawings

OTHER PUBLICATIONS

Dustin, M. et al, "A novel Mutagenesis Stategy Identifies Distantly Spaced Amino Acid Sequences the are Required for the Phosphorylation of Both the Oligosaccharides of Procathepsin D by N-Acetylglucosamine 1-Phosphotransferase," *The Journal of Biological Chemisty*, V.270, No. 1, pp. 170-179 (1995).

Guerout-Fleury, A. et al, "Plasmids for ectopic integration in *Bacillus subtilis*," *Gene*, 180, pp. 57-61 (1996).

Hall, Berry G., "Changes in the substrate specificities of an Enzyme during Directed Evolution of New Functions," *Biochemistry*, 20, pp. 4042-4049 (1981).

Horton, R. M. et al, "Engineering hybrid genes without the use of restriction enzymes: gene splicing by overlap extension," *Gene*, 77, pp. 61-68 (1989).

Iglesias, A. et al, "Plasmid Transformation in *Bacillus subtilis*: Symmetry of gene conversion in Transformation with a Hybrid Plasmid Containing Chromosomal DNA," *Mol Gen Genet*, 189, pp. 73-76 (1983).

Jansen, R. et al, "Disruption of phase during PCR amplification and cloning of heterozygous target sequences," *Nucleic Acids Research*, V. 18, No. 17 pp. 5153-5156 (1990).

Judo, M. et al, "Stimulation and suppression of PCR-mediated recombination," *Nucleic Acids Research*, vol. 26, No. 7, pp. 1819-1825 (1998).

Kuijper et al., "Functional cloning vectors for use in directional cDNA cloning using cohesive ends produces with T4 DNA polymerase," *GENE*, issue 06325, pp. 147-155 (1992).

Lebedenko, et al., "Method of artificial DNA splicing by directed ligation (SDL)," *Nucleic Acids Research*, V. 19, N. 24, pp. 6757-6761 (1991).

Ling et al., "Approaches to DNA Mutagenesis An Overview," *Analytical Biochemistry*, V. 254, 157-178 (1997) Article No. AB972428.

Kuchner, O. et al, "Directed evolution of enzyme catalysts," *TIB Tech*, vol. 15, 9 pages (1997).

Markland et al., "Iterative Optimization of High-Affinity Protease Inhibitors Using Phage Display. 1 Plasmin," *Biochemistry*, V. 35, pp. 8045-8057 (1996).

Marton, A. et al, "DNA nicking favors PCR recombination," *Nucleic Acids Research*, vol. 19, No. 9, pp. 2423-2426 (1991).

Merino et al., "A General, PCR-Based Method for Single or Combinatorial Oligonucleotide-Directed Mutagenesis on pUC/M13 Vectors," *BioFeedback*, V. 12, No. 4, pp. 508-510, (1992).

Meyerhans, A. et al, "DNA recombination during PCR," *Nucleic Acids Research*, vol. 18, No. 7, pp. 1687-1691 (1990).

Michel, B. et al, "Intramolecular recombination during plasmid transformation of *Bacillus subtilis* competent cells," *The EMBO Journal*, vol. 1, No. 12, pp. 1565-1571 (1982).

Michel, B. et al, "Intermolecular recombination during Transformation of *Bacillus subtilis* Competent Cells by Monomeric and Dimeric Plasmids," *Plasmid*, 10, pp. 1-10 (1983).

Ness, J. et al, "DNA shuffling of subgenomic sequences of subtilisin," *Nature Biotechnology*, vol. 17, pp. 893-896 (1999).

Niaudet, B. et al, "Insertional mutagensis in *Bacillus subtilis*: mechanism and use in gene cloning," *Gene*, 19, pp. 277-284 (1982).

Noirot, M.-A. et al, "Plasmid Replication Stimulates DNA Recombination in *Bacillus subtilis*," *J. Mol. Biol.*, 196, pp. 39-48 (1987).

Odelberg, S. et al, "Template-switching during DNA synthesis by *Thermus aquaticus* DNA polymerase 1," *Nucleic Acids Research*, vol. 23, No. 11, pp. 2049-2057 (1995).

Osuna et al., "Combinatorial mutagenesis of three major groove-contacting residues of EcoRI: single and double amino acid replacements retaining methyltransferase-sensitive activities," *GENE*, v. 106 pp. 7-12 (1991).

Paabo, S. et al, "DNA Damage Promotes Jumping between Templates during Enzymatic Amplification," *The Journal of Biological Chemistry*, vol. 265, No. 8, pp. 4718-4727 (1990).

Padgett et al., "Creating seamless junctions independent of restriction sites in PCR cloning," *GENE*, v. 168 pp. 31-35, (1996).

Peck, Joel R., "A Ruby in the Rubbish: Beneficial Mutations, Deleterious Mutations and the Evolution of Sex," *Genetics*, 137, pp. 597-606 (1994).

Rudolph, C. et al, "Transformation of *Bacillus subtilis* by Single-Stranded Plasmid DNA," *Journal of Bacteriology*, vol. 165, No. 3, pp. 1015-1018 (1986).

Schulga, A. et al, "An approach to construction of Hybrid Polypeptide molecules-homologue recombination method," *Nucleic Acids Research*, vol. 22, No. 18, pp. 3808-3810 (1994).

Shao, Z. et al, "Random-priming in vitro recombination: an effective tool for directed evolution," *Nucleic Acids Research*, vol. 26, No. 2, pp. 681-683 (1998).

Shi, X.-B. et al, "Rapid PCR Construction of a Gene Containing Lym-1 Antibody Variable Regions," *PCR Methods and Applications*, pp. 46-53 (1993).

Stemmer, William P.C., "DNA shuffling by random fragmentation and reassembly: in vitro recombination for molecular evolution," *Proc. Natl. Acad. Sci. USA*, vol. 91, pp. 10747-10751 (1994).

Stemmer, William P.C., "Searching Sequence Space: Using recombination to search more efficiently and thoroughly instead of making bigger combinatorial libraries," *Bio/Technology*, vol. 13, pp. 549-553 (1995).

Stoker, "Cloning of PCR products after defined cohesive termini arecreated with T4 DNA polymerase," *Nucleic Acids Research*, V. 18, No. 14, pp. 4290, (1990).

Szybalski et al., "Class-IIS restriction enzymes—a review," *GENE*, v. 100, pp. 13-26 (1991).

Tawfik, D. et al, "Man-made cell-like compartments for molecular evolution," *Nature Biotechnology*, vol. 16, pp. 652-656 (1998).

Tseng, DNA Cloning without Restriction Enzyme and Ligase, *Research Report*, V. 27 No. 6 pp. 1240-1244, (1999).

Wu et al., Humanization of a Murine Monoclonal Antibody by Simultaneous Optimization of Framework and CDR Resides, *J. Mol. Biol.*, V. 294, pp. 151-162, (1999).

Young, Michael, "The Mechanism of Insertion of a Segment of Heterologous DNA into the Chromosome of *Bacillus subtilis*," *Journal of General Microbiology*, 129, pp. 1497-1512 (1983).

Zhang, J-H. et al, "Directed evolution of a fucosidase from a galactosidase by DNA shuffling and screening," *Proc. Natl. Acad. Sci. USA*, vol. 94, pp. 4504-4509 (1997).

Zhao, H. et al, "Optimization of DNA shuffling for high fidelity recombination," *Nucleic Acids Research*, vol. 25, No. 6, pp. 1307-1308 (1997).

Zhao, H. et al, "Molecular evolution by Staggered extension process (StEP) in vitro recombination," *Nature Biotechnology*, vol. 16, pp. 258-261 (1998).

METHODS FOR FORMING RECOMBINED NUCLEIC ACIDS

This is a Divisional of U.S. patent application Ser. No. 09/566,645, filed on May 8, 2000 now U.S. Pat. No. 6,534,292, issued on Mar. 14, 2003.

FIELD OF THE INVENTION

This invention is related to the generation of recombined nucleic acid molecules, and more particularly to providing a novel method including the generation of random fragments and the assembly of a recombined nucleic acid molecule using template fragments which have non-extendable ends.

BACKGROUND OF THE INVENTION

Recombining nucleic acids has useful applications such as finding sequences which produce products having improved or desired characteristics. In particular, it is useful to develop a method for the production of mutant proteins which method allowed for the development of large libraries of mutant nucleic acid sequences which were easily searched.

A variety of in vitro DNA recombination methods exist. Examples include those described in U.S. Pat. No. 5,605,793 and in U.S. Pat. No. 5,965,408. Generally, recombination methods depend on a step of making fragments, and a step of recombining the fragments. For example, U.S. Pat. No. 5,605,793 generally relies on fragmentation of double stranded DNA molecules by DNase I. U.S. Pat. No. 5,965,408 generally relies on the annealing of relatively short random primers to target genes and extending them with DNA polymerase. Each of these disclosures relies on polymerase chain reaction (PCR)-like thermocycling of fragments in the presence of DNA polymerase to recombine the fragments.

Generally, existing methods generate DNA fragments with functional 3' ends, which can be readily extended in the presence of complementary sequences. Thus, in one of the examples described above, a consequence of this feature is that fragments in the assembly or recombination step are independent from each other. The fragments can anneal to their complementary counterparts and get extended by DNA polymerase irrespectively of their position in the primary sequences of the gene—extension of different fragments occurs in parallel.

Although, a number of methods exist, it would generally be desirable to provide novel methods of recombining nucleic acids. Moreover, it would be desirable to provide a method of forming recombined nucleic acid molecules which took into account the position of a fragment relative to the primary or initial sequence from which it was fragmented. In particular, it would be desirable to provide methods of forming recombined nucleic acid molecules wherein a sequence was fragmented, and wherein the fragments were used as templates only, rather than as templates and primers for extension.

SUMMARY OF THE INVENTION

The present invention provides methods of forming recombined nucleic acid molecules. Generally, the methods involve providing or generating fragments, and using the fragments to form a recombined nucleic acid molecule. Preferably, the fragments come from at least two different initial sequences, and the recombined nucleic acid molecule has a sequence which differs from either of the initial sequences. As such, a large number of recombined nucleic acids can be formed which can be screened to identify a sequence which provides a molecule having a desired characteristic.

In one aspect of the invention, template fragments of at least one sequence, sometimes called the initial sequence, are provided. Preferably, the template fragments have non-extendable 3' ends. In a preferred embodiment, the template fragments are generated as described below. Moreover, the method comprises providing at least one primer, and reacting said primer and said template fragments under conditions to extend said primer to form said recombined nucleic acid molecule.

In preferred embodiments herein, the method is repeated until the recombined nucleic acid has been assembled to have the length of the sequence from which the fragments were formed. In one embodiment, at least two sequences which differ from each other are used. Preferably, the two sequences which differ from each other are homologs of one another. In one embodiment, the sequences are variants of the same naturally-occurring sequence. In preferred embodiments, the recombined nucleic acid has at least one fragment from each sequence such that the recombined nucleic acid molecule has a sequence which differs from either of said at least one sequence.

Additionally, vectors, host cells, recombinant nucleic acids, proteins, pools of nucleic acid molecules and screening assays are provided herein.

DETAILED DESCRIPTION OF THE INVENTION

Provided herein are methods of forming recombined nucleic acids. Generally, the methods involve providing or generating fragments of at least one sequence wherein the fragments have non-extendable ends. The fragments are then used as templates in the assembly of a recombined nucleic acid. Thus, the present invention provides novel methods of generating recombined nucleic acids which can then be used in a number of applications such as use in screening assays for desired characteristics.

In one aspect of the invention, template fragments of at least one sequence are provided. The template fragments have non-extendable ends as further described below. In one embodiment, the template fragments are reacted with a primer under conditions which allow extension of the primer. As such a reaction gets repeated, the primer becomes extended upon each repetition, however, the template fragments cannot be extended. Upon repetitions of the method, the primer continues to extend until a recombined nucleic acid molecule is formed which is the length of the sequence from which the template fragments were formed.

Thus in one aspect of the invention, at least one sequence is selected from which template fragments are based. The sequence can be any nucleic acid sequence and is sometimes referred to as the "initial sequence". Nucleic acids can include DNA, RNA, or a hybrid, where the nucleic acid contains any combination of deoxynucleotides, dideoxynucleotides and ribonucleotides, and any combination of bases, including uracil, adenine, thymine, cytosine, guanine, inosine, xathanine hypoxathanine, isocytosine, isoguanine, etc. Nucleic acid can further includes genomic DNA, in particular genomic DNA from eukaryotes, prokaryotes, archaebacteria, and viruses, cDNA, synthetic DNA and oligonucleotides including sense and anti-sense nucleic acids.

The initial sequence can be any sequence including genes, operons or metabolic pathways, or chromosomes.

In a preferred embodiment more than one sequence is used as an initial sequence. In this embodiment, a heterogenous population of nucleic acid molecules may be used. The terms "population" or "library" or grammatical equivalents thereof, as used herein, generally mean a collection of components such as nucleic acids, nucleic acid fragments, proteins, vectors, constructs, cells, etc. Usually, a population of the invention comprises from at least two components to $10^9$ components. Preferred are populations comprising from at least 10 components to $10^8$ components, more preferred are populations comprising from at least 50 components to $10^7$ components and most preferred are populations comprising from at least 100 components to $10^6$ components. Preferably, within each family of components, e.g., nucleic acids, the family members are related, but differ in at least one aspect, e.g., in their sequence, i.e., they are not identical.

The initial sequence can be any nucleic acid sequence including naturally occurring sequences and variants thereof. By "naturally occurring", "wild type" or grammatical equivalents thereof, is meant a nucleic acid sequence or an amino acid sequence that is found in nature and in one embodiment, includes naturally occurring allelic variations. Alternatively, the sequence is a non-naturally occurring nucleic acid. By "non-naturally occurring", or grammatical equivalents thereof, is meant a nucleic acid sequence or an amino acid sequence that is not found in nature.

Preferably, the initial sequences are a mixture of naturally occurring and non-naturally occurring nucleic acids.

In one aspect of this embodiment, the initial sequence is a variant of a naturally occurring nucleic acid. A "variant" or grammatical equivalents thereof, refers to a component that is altered at one or more sites with respect to a corresponding naturally occurring component. Thus, a nucleic acid variant (or variant nucleic acid) comprises a nucleotide sequence that is altered by one or more nucleotides when compared to a nucleotide sequence of a naturally occurring nucleic acid or to a nucleotide sequence of a non-naturally-occurring nucleic acid. Accordingly, a protein variant (or variant protein) comprises an amino acid sequence that is altered by one or more amino acid residues when compared to an amino acid sequence of a naturally occurring protein or to an amino acid sequence of a non-naturally-occurring protein. In one embodiment, a variant has one or more deletions, substitutions, insertions, or combinations thereof.

In a preferred embodiment of the invention, a population of sequences comprises a naturally-occurring nucleic acid, homologs, naturally occurring allelic variations thereof as well as random and site-directed variants. Wherein each initial sequence is based on the same nucleic acid, being variants or homologs thereof, etc., the sequences are said to be related or a family. In one aspect of the invention, homolog refers to a gene or protein which is identified as functionally equivalent but produced in a different species.

In one aspect of the invention, a population of sequences is generated by mutagenesis. The mutagenesis methods employed may be site-directed or random and are generally known in the art. Alternatively, error-prone PCR can be used to generate the initial sequences. Other methods for obtaining initial sequences can be used, such as using mutator strains, chemical mutagenesis or irradiation with X-rays or ultraviolet light using methods as known in the art.

In one aspect of the invention, the initial sequences or fragments as further discussed below can be represented at about the same ratio. In another aspect of this embodiment, one sequence or fragment is over-represented. Preferred ratios include 1:1 to 1:100, or more preferably, 1:1 to 1:40. Each sequence or variant in a population may be present in a different molar ratio in the population.

In one embodiment, only one initial sequence is used. In this embodiment, the template fragments generated may comprise mutations, such as one or more nucleotide substitutions, additions, deletions, truncations or combinations thereof. Such mutations may be introduced during the step of generating the template fragments or after formation of the fragments. This can be done using methods known in the art including, but not limited to random or site-directed mutagenesis, error-prone PCR or the inclusion of mutagenic agents in the step of generating the template fragments.

In one embodiment, the template fragments are generally complementary to the initial sequence, such that the intial sequence serves as a template to the template fragments. However, it is understood that further rounds of replication can produce a fragment with the same sequence as the initial sequence, rather than being complementary thereto. The initial sequence can be fragmented or be of any length. The template fragments can be generated from an intact initial sequence, or from a fragmented initial sequence.

In another embodiment, the initial sequence is modified to have non-extendable ends and serves as the template fragments. Preferably, the initial sequence is fragmented.

The number of different specific nucleic acid fragments generated by fragmenting an initial sequence or in the generation of the template fragments will depend on the size of the initial sequence. The number of template fragments of a sequence may be at least 2, preferably at least about 2 to 10 and may be at least about 20, preferably at least about 50, more preferably at last about 100 and most preferably at least about $10^3$. Wherein the sequence is an operon or a chromosome, the fragments may be in the range of at least about 1000, more preferably at least about $10^4$, more preferably at least about $10^5$ and most preferably at least about $10^6$. The fragments may be of different sizes and are preferably at least about 15 bp and may be at least about 50 bp, 100 bp, 200 bp, 300 bp, 500 bp, 1 kb, up to 5 kb.

In one embodiment, the initial sequence is randomly fragmented. Random fragmentation can be done by using enzymes including, but not limited to DNAsel [Liao, J. Biol. Chem. 249:2354 (1974); Matsuda and Ogoshi J. Biochem. 59:230 (1966); Hong, Methods Enzymol. 155:93 (1987)], P1 nuclease [Furuichi and Miura, Nature 253:374 (1975)], S1 nuclease [Noll, Nature 251:249 (1974)], T7 endonuclease [Center et al., Proc. Natl. Acad. Sci. U.S.A. 65:242 (1970); de Massy et al., J. Mol. Biol. 193:359 (1987)], mung bean nuclease, RNAse or combinations thereof, or in combinations with intercalating agents, such as ethidiumbromide. In one embodiment, random fragmentation of the sequence may be by shearing, and includes, but is not limited to sonication of intitial sequences and passage of the initial sequences through a tube having a small orifice, such as a needle.

In another embodiment, fragmentation is by the use of one or more restriction endonucleases [see Brown, *Molecular Biology LabFax*, BIOS Scientific Publishers Limited; Information Press Ltd, Oxford, UK, 1991) and REBASE (restriction enzyme data base), a comprehensive database of restriction enzymes, including type IIs restriction enzymes (Roberts and Macelis, Nucleic Acids Res. 26(1):338–350 (1998)]. In one embodiment, a population of sequences is released from a cloning vector. Optionally the released population of sequences is purified away from the cloning vector using methods including, but not limited to centrifugation, sizing filtration, and gel electrophoresis.

The fragments may be size selected. Procedures for size selection include, but are not limited to, preparative gel electrophoreses and centrifugation techniques. These methods are known in the art [e.g., see Sambrook et al., *Molecular Cloning: A Laboratory Manual* (2nd ed.) Vol. 1–3, Cold Spring Harbor Laboratory Press, New York (1989)].

In one embodiment, double-stranded sequences used herein may be denatured. Generation of single-stranded DNAs can be done in a variety of ways, including, but not limited to thermal denaturation, alkaline treatment or exonuclease treatment. Commercially available exonucleases include, but are not limited to λ exonuclease, bacteriophage T7 gene 6 exonuclease, Bal 31 nuclease, and exonuclease III [see Sambrook et al., *Molecular Cloning: A Laboratory Manual* (2nd ed.) Vol. 1–3, Cold Spring Harbor Laboratory Press, New York (1989); Brown, *Molecular Biology Lab-Fax*, BIOS Scientific Publishers Limited; Information Press Ltd, Oxford, UK, 1991)]. The exonuclease is added to the double-stranded sequence and is incubated, according to the recommendations of the supplier, under conditions sufficient for the successive removal of nucleotides from the double-stranded sequence.

In one aspect of this embodiment, the template fragment is generated using a DNA polymerase. In this embodiment, the template fragment generated comprises DNA. DNA polymerases include, but are not limited to DNA polymerase I (Kornberg polymerase), DNA polymerase I (Klenow fragment), T4 DNA polymerase, T7 DNA polymerase, Taq DNA polymerase, micrococcal DNA polymerase, and eukaryotic DNA polymerases, such as alpha DNA polymerase, etc.

In another aspect of this embodiment, the initial sequence is RNA and the template fragment is generated using a reverse transcriptase. In this embodiment, the template fragment generated comprises RNA. Reverse transcriptases include, but are not limited to AMV (avian myeloblastosis virus) reverse transcriptase, M-MuLV (Moloney murine leukemia virus) reverse transcriptase, etc.

In a further aspect of this embodiment, the initial sequence is DNA and the template fragment is generated using a RNA polymerase. In this embodiment, the template fragment generated comprises RNA. RNA polymerases include but are not limited to *E.coli* RNA polymerase, SP6 RNA polymerase, T3 RNA polymerase, T7 RNA polymerase, and eukaryotic RNA polymerases, such as wheat germ RNA polymerase II, etc.

In one embodiment, the step of generating the template fragments is performed only once. In this embodiment, non-thermophilic polymerases, as those described above, can be used.

In another embodiment, the step of generating the template fragments is performed more than once. In this embodiment, the generation of template fragments comprises multiple rounds of denaturation and annealing (or hybridizing) of the oligonucleotide. In this embodiment, the preferred polymerases are thermostable polymerases, such as, but not limited to Taq DNA polymerase, Pfu DNA polymerase, etc.

In another embodiment, wherein binding sites or promoters for polymerases are employed in the generation of the template fragments, multiple copies of template fragments are usually generated without denaturation.

In one embodiment of this invention, the synthesis of the template fragment is primer dependent. In this embodiment, one or more oligonucleotides are added to the initial sequence. The term "oligonucleotide" or grammatical equivalents thereof, as used herein, refers to a nucleic acid sequence of at least about 4 or 6 nucleotides to about 60 nucleotides, preferably about 15–30 nucleotides, and more preferably about 20–25 nucleotides. A primer is an oligonucleotide which can anneal to another nucleic acid and which can use said nucleic acid as a template. To be able to use a nucleic acid as a template means that the nucleic acid has at least one nucleotide which the primer lacks such that the primer can be extended using the nucleic acid as a template. In one embodiment, the primers are random. Primers may also be generated by fragmentation of the initial sequence.

In another embodiment, template fragments are generated without the use of primers. In this embodiment, the initial sequence is fragmented and modified to have non-extendable ends as described below. In another embodiment, template fragments are generated using sequences that are operably linked to binding sites or promoters for DNA or RNA polymerases.

The template fragments may be of different sizes and are preferably at least about 15 bp and may be at least about 50 bp, 100 bp, 200 bp, 300 bp, 500 bp, 1 kb, 5 kb, 10 kb, or preferably larger in some embodiments. The size of the template fragments can be controlled in a variety of ways.

In one aspect, the template fragments are synthesized under conditions, wherein the synthesis of the template fragment initiates at the position where a primer annealed to the sequence or at a polymerase binding site and proceeds to the end of the sequence. These conditions include e.g., non-limiting nucleotide concentrations and optimal reaction conditions as recommended by the supplier of the respective enzymes used herein. Thus, the size of the template fragment corresponds substantially to the size of the initial sequence.

In another aspect, the size of template fragments is controlled kinetically by e.g., limiting reaction time. The concentrations of salt in the buffer and nucleotides may also be adjusted to obtain a desired size of template fragments.

In a further aspect of this embodiment, inhibitors of nucleic acid synthesis may be added at any time during the generation of the template fragments to control the size of the template fragments. Suitable inhibitors include, but are not limited to actinomycin D, α-amanitin, bleomycin, chloramphenicol, 5-fluorouracil, mitomycin C, rifampicin, etc.

The template fragments generated on a sequence or on fragments thereof thus are of random size and are of random position with respect to the sequence or fragments thereof. The degree of randomness of template fragments can be increased by employing multiple rounds of generating template fragments on the same sequence or fragments thereof as described above.

In a preferred embodiment of this invention, the template fragments have non-extendable ends. By non-endable end means that the nucleic acid cannot be extended. For example, standard polymerase reactions generally add a nucleic acid to the 3' end of the molecule. A non-extendable end prevents extension of the nucleic acid.

In one aspect of this embodiment the 3' non-extendable end of the template fragment comprises a terminator molecule. By "terminator molecule" is meant any molecule which prevents extension under conditions which would normally provide extension. The terminator molecule may be a variety of chemical agents added to the sequence, or may be a nucleic acid analog. For example, an agent may be added or an analog which blocks or does not have the oxygen of the terminal OH group, or blocks or does not have the terminal OH group.

In a preferred embodiment, the terminator molecule is a dideoxyribonucleotide (ddNTP). A ddNTP differs from a deoxynucleotide (dNTP) by having at the 3' position in the ribose backbone a hydrogen (H) group instead of a hydroxyl (OH) group. Incorporation of a dideoxynucleotide into a nucleic acid blocks further extension of the nucleic acid, as the dideoxynucleotide lacks the 3' OH group that is required for this process. Suitable ddNTPs include, but are not limited to ddATP, ddCTP, ddGTP, and ddTTP.

In another preferred aspect of this embodiment, any nucleotide analog that usually can be incorporated into a nucleic acid can be used in the present invention as long as it comprises a group, such as a 3' H group that impairs further extension of the nucleic acid by a polymerase. Several nucleotide analogs are described (e.g., see, in Rawls, C & E News Jun. 2, 1997 page 35; in Brown, Molecular Biology LabFax, BIOS Scientific Publishers Limited; Information Press Ltd, Oxford, UK, 1991; these references are hereby expressly incorporated by reference). These nucleotide analogs include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, hypoxanthine, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, orotic acid, and 2,6-diaminopurine.

In one embodiment, the terminator molecule is added during the generation of the template fragments in a polymerase reaction. The presence of the terminator molecule in the extension reaction further controls the degree of extension and thereby the size of the template fragment.

For example, upon increasing the concentration of terminators with respect to the concentration of dNTPs, the probability of their incorporation into the growing nucleic acid is increased, which in turn leads to the generation of smaller template fragments. Accordingly, upon decreasing the concentration of terminator molecules with respect to the concentration of dNTPs, the probability of their incorporation into the growing nucleic acid is reduced, which in turn leads to the generation of larger template fragments.

In another preferred embodiment, the terminator molecule is added to the 3' end of the template fragment by a terminal deoxynucleotidyl transferase (Tdt). Tdt is a template-independent DNA polymerase, that can add deoxynucleotides and dideoxynucleotides to a 3'-OH terminus on single-stranded DNA and on double-stranded DNA [Deng and Wu, Nucleic Acids Res. 9:4173 (1981); Michelson and Orkin, J. Biol. Chem. 257:14773 (1982)]. Thus, in one embodiment, the template fragments can be double-stranded and then denatured.

In preferred embodiments, the template fragments have overlapping ends. By overlapping ends means that if the fragments were aligned sequentially from the 5' end toward the 3' end to form a first, second and third fragment, respectively, the 3' end of the first fragment would be identical to the 5' end of the second fragment, and the 3' end of the second fragment would be identical to the 5' end of the third fragment. Depending on the orientation of the fragments in respect to the initial sequence, the converse may be the case. The overlapping ends are preferably long enough to serve as primers to a complementary sequence.

In a preferred embodiment, the template fragments are single-stranded DNA or RNA. Wherein the template fragments were polymerized on another template such as the initial sequence, the template fragments are purified away from the sequence or other extraneous DNA, such as vector DNA and primers.

In one aspect of the invention, at least one primer is added to at least one template fragment, and the primer and the template fragment(s) are reacted under conditions to extend the primer to form a recombined nucleic acid molecule. In a preferred embodiment, the primer added to the template fragments is a primer which anneals to the 3' end of the template fragment. Preferably, the template fragment corresponds to the 5' end of the initial sequence. In other embodiments, other primers can be used such as those discussed above. Preferably primers which anneal to fragments towards the center of and/or the 3' end of the initial sequence or sequence complementary thereto are used, preferably in combination with primers which extend from the 5' end of the initial sequence.

In another embodiment, one or more of the template fragments act as a primer and thus, no additional primers are added.

Conditions which allow a primer to extend on a template generally include a polymerase, nucleotides and a suitable buffer. The nucleic acid which is generated on the template fragments comprises a 3'-OH group, which can be further extended. Preferably, the extension proceeds until the polymerase reaches the 5' end of the template fragment. However, the extent of the extension reaction may be controlled, for example, as described above.

Thus, in one embodiment, at least one template fragment is reacted with a primer under conditions suitable for extension of said primer, wherein said template fragment has a non-extendable 3' end.

In one aspect of the invention, the process of extending the primer is subjected to repetitions. In each case, the primers will extend but the template fragments will not. Thus, for example, in the first round of an extension or polymerase reaction, a primer at the 3' end of a template fragment based on the 5' end of the initial sequence, e.g., primer "A", will produce a nucleic acid complementary to the template fragment. At the end of the polymerase reaction, primer A has an extended 3' end complementary to the template fragment. The extended primer A has an extendable 3' end. In a subsequent round of extension, primer A will anneal with another template fragment wherein the 3' end of the extended primer A is complementary to the 3' end of a template fragment, preferably the next sequential overlapping end of a template fragment. This process can be repeated until the primer is extended to be the length of the initial sequence.

The term "assembly" or grammatical equivalents thereof, as used herein, means combining one or more nucleic acid molecules to form one contiguous nucleic acid molecule. The assembly step comprises forming a nucleic acid which is the complement to at least two template fragments. Preferably, the two template fragments have overlapping ends and are sequential relative to the initial sequence.

Assembly is generally based upon the overlapping ends of the template fragments which lead to an extended primer complementary to the sequential template fragment. By "sequential" is meant the next nucleic acid sequence, preferably in a 5' to 3' direction in relation to the initial sequence. The annealing reaction is based on substantial complementation between sequences and is known in the art.

"Recombination", "recombining", or generating a "recombined" nucleic acid is generally the assembly of two or more template fragments wherein the assembly gives a different sequence than the corresponding sequence of the initial sequence(s) from which the template fragments are based.

It is understood that any one fragment having a non-extendable end can be used as a template fragment. Thus, one embodiment includes polymerizing a sequence using a template having non-extendable ends. Preferably, the template is a variant, or a variant is generated during or after polymerization.

The term "recombinant nucleic acid" or grammatical equivalents thereof generally refers to any nucleic acid formed or substantially purified in vitro.

Preferably the extension cycle or round is repeated at least 2 times, more preferably up to 5 times, more preferably up to 10 times, and most preferably up to 100 times or more. The cycles of assembly and recombining may be reiterated until a recombined nucleic acid of similar length as the initial sequence is generated or until a full-length gene is generated. In some embodiments, shorter recombined nucleic acids may be preferred.

In one embodiment, the recombined nucleic acid or the full-length gene generated according to one of the methods described above, is amplified. The terms "amplification" or "amplify" or grammatical equivalents thereof, as used herein, refer to the production of additional copies of a nucleic acid sequence and is generally carried out using the polymerase chain reaction (PCR). PCR technologies are well known in the art (e.g., see Dieffenbach and Dveksler in PCR Primer, A Laboratory Manual, Cold Spring Harbor Press, Princeton, N.Y.). The recombined nucleic acid can be amplified by polymerase chain reaction at any time during the assembly and recombining cycles.

Thus, the invention provides a method for the generation of a recombined nucleic acid. Preferably, the recombined nucleic acid has a sequence which is different from the initial sequence(s). The sequence of the recombined nucleic acid may differ by having at least one section of sequence replaced by a fragment of a variant or homolog in accordance with the methods provided herein. In an alternative embodiment, the sequence may differ by having sections within one initial sequence rearranged in a different order. This may happen wherein there are repeats in the sequence which allow for annealing between sequences which are not sequential.

In one embodiment, the product encoded by the recombined nucleic acid retains the function of the wild type protein, such as catalytic activity, but has an altered property such as further discussed below. A recombined nucleic acid or protein as used herein refers to any sequence which has been manipulated to contain at least a portion of another molecule, ranging from at least one residue to as many as the entire sequence minus one residue.

Generally, the methods of the invention are useful for the generation of novel recombined nucleic acids. These novel nucleic acids may encode useful proteins, such as novel receptors, ligands, antibodies and enzymes. These novel nucleic acids may also comprise hybrid nucleic acids, wherein, for example, 5' untranslated regions of genes, 3' untranslated regions of genes, introns, exons, promoter regions, enhancer regions and other regulatory sequences for gene expression, such as dominant control regions, are recombined.

Thus, the methods of the invention provide for the formation of recombined nucleic acids ranging from 50–100 bp to several Mbp. Recombining and assembly of sequences using the method of the invention, can be useful when sequences lack convenient or any restriction sites. Additionally, the methods herein generally favor the combination of sequences in a sequential order corresponding to the order of the initial sequence.

The steps of the methods provided herein may constitute a cycle which favor direction toward desirable mutations leading to desirable traits or phenotypes. The recombined nucleic acid may be cloned into a vector, propagated and screened for a species or first subpopulation with a desired property. This results in the identification and isolation of, or enrichment for, a recombined nucleic acid encoding a polypeptide that has acquired a desired property.

According to one embodiment of the present invention, at least two initial sequences are recombined at the same time. However, preferably any number of initial sequences may be assembled or recombined at the same time. This is advantageous because a large number of different variants can be made rapidly without iterative procedures.

In one embodiment, described above, a population of recombined nucleic acids is subjected to reiterated assembly and recombining without prior cloning into a vector, propagation or screening to identify a species with a desired property.

The recombined nucleic acid may be used in screening assays for desired characteristics in the nucleic acid or in the polypeptide encoded by the nucleic acid. Additionally, the recombined nucleic acid is cloned into a vector at any time after an assembly and recombining step.

As outlined above, the invention provides recombined nucleic acids encoding polypeptides. The recombined nucleic acids and the polypeptides preferably have at least one property, which is different from the same property of the corresponding sequence or corresponding naturally occurring polypeptide. The properties described herein may also be referred to as biological activities.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, Km, kcat, Kcat/km ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

As used herein, the term "screening" has its usual meaning in the art and is, in general a multi-step process. In the first step, a recombined nucleic acid or variant polypeptide is provided. In the second step, a property of the recombined nucleic acid or variant polypeptide is determined. In the third step, the determined property is compared to a property of the corresponding naturally occurring nucleic acid, to the property of the corresponding naturally occurring polypeptide or to the property of the starting material (e.g., the initial sequence) for the generation of the recombined nucleic acid. The latter may also be a synthetic DNA.

It will be apparent to the skilled artisan that the screening for an altered property depends entirely upon the property of the starting material for the generation of the recombined nucleic acid. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after recombination, wherein a change indicates an alteration. Preferably, the screens are performed in a high-throughput manner, including multiple samples being screened simultaneously, including, but not limited to assays utilizing chips, phage display, and multiple substrates and/or indicators.

Unless otherwise specified, a change in any of the above-listed properties, when comparing the property of a recombined nucleic acid or variant polypeptide to the property of a naturally occurring nucleic acid or naturally occurring protein is preferably at least a 10% or 20%, more preferably, 50%, more preferably at least a 2-fold, 3-fold, 10-fold or 100-fold increase or decrease.

A change in substrate specificity is defined as a difference between the kcat/Km ratio of the naturally occurring protein and that of the variant thereof. The kcat/Km ratio is generally a measure of catalytic efficiency. Generally, the objective will be to generate variants of naturally occurring proteins with greater (numerically large) kcat/Km ratio for a given substrate when compared to that of the naturally occurring protein, thereby enabling the use of the protein to more efficiently act on a target substrate. However, it may be desirable to decrease efficiency. An increase in kcat/Km ratio for one substrate may be accompanied by a reduction in kcat/Km ratio for another substrate. This is a shift in substrate specificity and variants of naturally occurring proteins exhibiting such shifts have utility where the naturally occurring protein is undesirable, e.g., to prevent undesired hydrolysis of a particular substrate in an admixture of substrates. Km and kcat are measured in accordance with known procedures.

A change in oxidative stability is evidenced by at least about 10% or 20%, more preferably at least 50% increase of enzyme activity when exposed to various oxidizing conditions. Such oxidizing conditions include, but are not limited to exposure of the protein to the organic oxidant diperdodecanoic acid (DPDA). Oxidative stability is measured by known procedures.

A change in alkaline stability is evidenced by at least about a 5% or greater increase or decrease (preferably increase) in the half life of the enzymatic activity of a variant of a naturally occurring protein when compared to that of the naturally occurring protein. In the case of e.g., subtilisins, alkaline stability can be measured as a function of autoproteolytic degradation of subtilisin at alkaline pH, e.g., 0.1M sodium phosphate, pH 12 at 25° C. or 30° C. Generally, alkaline stability is measured by known procedures.

A change in thermal stability is evidenced by at least about a 5% or greater increase or decrease (preferably increase) in the half life of the catalytic activity of a variant of naturally occurring protein when exposed to a relatively high temperature and neutral pH as compared to that of the naturally occurring protein. In the case of e.g., subtilisins, thermal stability can be measured as a function of autoproteolytic degradation of subtilisin at elevated temperatures and neutral pH, e.g., 2 mM calcium chloride, 50 mM MOPS, pH 7.0 at 59° C. Generally, thermal stability is measured by known procedures.

Receptor variants, for example are experimentally tested and validated in in vivo and in in vitro assays. Suitable assays include, but are not limited to, e.g., examining their binding affinity to natural ligands and to high affinity agonists and/or antagonists. In addition to cell-free biochemical affinity tests, quantitative comparison are made comparing kinetic and equilibrium binding constants for the natural ligand to the naturally occurring receptor and to the receptor variants. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. For most receptors described herein, the binding constant between a natural ligand and its corresponding naturally occurring receptor is well documented in the literature. Comparisons with the corresponding naturally occurring receptors are made in order to evaluate the sensitivity and specificity of the receptor variants. Preferably, binding affinity to natural ligands and agonists is expected to increase relative to the naturally occurring receptor, while antagonist affinity should decrease. Receptor variants with higher affinity to antagonists relative to the non-naturally occurring receptors may also be generated by the methods of the invention.

Similarly, ligand variants, for example are experimentally tested and validated in in vivo and in in vitro assays. Suitable assays include, but are not limited to, e.g., examining their binding affinity to natural receptors and to high affinity agonists and/or antagonists. In addition to cell-free biochemical affinity tests, quantitative comparison are made comparing kinetic and equilibrium binding constants for the natural receptor to the naturally occurring ligand and to the ligand variants. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. For most ligands described herein, the binding constant between a natural receptor and its corresponding naturally occurring ligand is well documented in the literature. Comparisons with the corresponding naturally occurring ligands are made in order to evaluate the sensitivity and specificity of the ligand variants. Preferably, binding affinity to natural receptors and agonists is expected to increase relative to the naturally occurring ligand, while antagonist affinity should decrease. Ligand variants with higher affinity to antagonists relative to the non-naturally occurring ligands may also be generated by the methods of the invention.

In one embodiment of the invention, at least one sequence encodes a protein.

By "protein" herein is meant at least two covalently attached amino acids, which may include proteins, polypeptides, oligopeptides and peptides. The protein may be a naturally occurring proteins, a variant of a naturally occurring protein or a synthetic protein. The protein may be made up of naturally occurring amino acids and peptide bonds, or synthetic peptidomimetic structures, generally depending on the method of synthesis. Thus "amino acid", in one embodiment, means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. Stereoisomers of the twenty conventional amino acids, unnatural amino acids such as α,α-disubstituted amino acids, N-alkyl amino acids, lactic acid, and other unconventional amino acids may also be suitable components for proteins of the present invention. Examples of unconventional amino acids include, but are not limited to: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids. If non-naturally occurring side chains are used, non-amino acid substituents may be used, for example to prevent or retard in vivo degradations. Proteins including non-naturally occurring amino acids may be synthesized or in some cases, made by recombinant methods; see van Hest et al., FEBS Lett. 428:(1–2) 68–70 (1998); and Tang et al., Abstr. Pap. Am. Chem. S218:U138-U138 Part 2 (1999), both of which are expressly incorporated by reference herein.

A "recombinant protein", as outlined further below, or grammatical equivalents thereof, as used herein, refer to a protein made using recombinant techniques, i.e. through the expression of a recombined nucleic acid or recombinant nucleic acid as depicted above or by being substantially purified from its natural environment. A recombined or variant protein is distinguished from a naturally occurring protein by at least one or more characteristics. For example, the recombined or variant protein may be isolated or purified away from some or all of the proteins and compounds with which it is normally associated in its wild type host, and thus may be substantially pure. For example, an isolated recombined or variant protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. As used herein, "substantially pure" means an object species (such as a protein or nucleic acid) is the predominant species present (i.e., on a molar basis it is more abundant than any other individual species in a composition), and preferably a substantially purified fraction is a composition, wherein the object species comprises at least about 50% (on a molar basis) of all macromolecular species present. Generally, a substantially pure composition will comprise more than about 80 to 90 percent of all macromolecular species present in the composition. Isolated nucleic acids and proteins are those taken from their native environment. Most preferably, the object species is purified to essential homogeneity (macromolecular contaminant species cannot be detected in the composition by conventional detection methods), wherein the composition consists essentially of a single macromolecular species.

Included within this definition are proteins whose amino acid sequence is altered by one or more amino acids when compared to the sequence of a naturally occurring protein.

The definition also includes the production of a protein from one organism in a different organism or host cell. Alternatively, the recombined or variant protein may be made at a significantly higher concentration than is normally seen, through the use of a inducible promoter or high expression promoter, such that the recombined or variant protein is made at increased concentration levels. Furthermore, all of the recombined or variant proteins outlined herein are in a form not normally found in nature, as they may contain amino acid substitutions, insertions and deletions, with substitutions being preferred.

The nucleic acids may be from any number of eukaryotic or prokaryotic organisms or from archaebacteria. Particularly preferred are nucleic acids from mammals. Suitable mammals include, but are not limited to, rodents (rats, mice, hamsters, guinea pigs, etc.), primates, farm animals (including sheep, goats, pigs, cows, horses, etc) and in the most preferred embodiment, from humans. Other suitable examples of eukaryotic organisms include plant cells, such as maize, rice, wheat, cotton, soybean, sugarcane, tobacco, and arabidopsis; fish, algae, yeast, such as *Saccharomyces cerevisiae;* Aspergillus and other filamentous fungi; and tissue culture cells from avian or mammalian origins. Also preferred are nucleic acids from prokaryotic organisms. Suitable examples of prokaryotic organisms include gram negative organisms and gram positive organisms. Specifically included are enterobacteriaciae bacteria, *pseudomonas, micrococcus, corynebacteria, bacillus, lactobacilli, streptomyces,* and *agrobacterium.* Polynucleotides encoding proteins and enzymes isolated from extremophilic organisms, including, but not limited to *hyperthermophiles, psychrophiles, psychrotrophs, halophiles, barophiles* and *acidophiles,* are particularly preferred. Such enzymes may function at temperatures above 100° C. in terrestrial hot springs and deep sea thermal vents, at temperatures below 0° C. in arctic waters, in the saturated salt environment of the Dead Sea, at pH values at around 0 in coal deposits and geothermal sulfur-rich springs, or at pH values greater than 11 in sewage sludge.

The proteins can be intracellular proteins, extracellular proteins, secreted proteins, enzymes, ligands, receptors, antibodies or portions thereof.

In a preferred embodiment of the invention, the first double-stranded DNA encodes all or a portion of an enzyme. By "enzyme" herein is meant any of a group of proteins that catalyzes a chemical reaction.

Enzymes include, but are not limited to (i) oxidoreductases; (ii) transferases, comprising transferase transferring one-carbon groups (e.g., methyltransferases, hydroxymethyl-, formyl-, and related transferases, carboxyl- and carbamoyltransferases, amidinotransferases) transferases transferring aldehydic or ketonic residues, acyltransferases (e.g., acyltransferases, aminoacyltransferas), glycosyltransferases (e.g., hexosyltransferases, pentosyltransferases), transferases transferring alkyl or related groups, transferases transferring nitrogenous groups (e.g., aminotransferases, oximinotransferases), transferases transferring phosphoruscontaining groups (e.g., phosphotransferases, pyrophosphotransferases, nucleotidyltransferases), transferases transferring sulfur-containing groups (e.g., sulfurtransferases, sulfotransferases, CoA-transferases), (iii) Hydrolases comprising hydrolases acting on ester bonds (e.g., carboxylic ester hydrolases, thioester hydrolases, phosphoric monoester hydrolases, phosphoric diester hydrolases, triphosphoric monoester hydrolases, sulfuric ester hydrolases), hydrolases acting on glycosyl compounds (e.g., glycoside hydrolases, hydrolyzing N-glycosyl compounds, hydrolyzing S-glycosyl compound), hydrolases acting on ether bonds (e.g., thioether hydrolases), hydrolases acting on peptide bonds (e.g., α-aminoacyl-peptide hydrolases, peptidyl-amino acid hydrolases, dipeptide hydrolases, peptidyl-peptide hydrolases), hydrolases acting on C—N bonds other than peptide bonds, hydrolases acting on acid-anhydride bonds, hydrolases acting on C—C bonds, hydrolases acting on halide bonds, hydrolases acting on P—N bonds, (iv) lyases comprising carbon-carbon lyases (e.g., carboxy-lyases, aldehyde-lyases, ketoacid-lyases), carbon-oxygen lyases (e.g., hydro-lyases, other carbon-oxygen lyases), carbon-nitrogen lyases (e.g., ammonia-lyases, amidine-lyases), carbon-sulfur lyases, carbon-halide lyases, other lyases, (v) isomerases comprising racemases and epimerases, cis-trans isomerases, intramolecular oxidoreductases, intramolecular transferases, intramolecular lyases, other isomerases, (vi) ligases or synthetases comprising ligases or synthetases forming C—O bonds, forming C—S bonds, forming C—N bonds, forming C—C bonds.

Particularly preferred are carbonyl hydrolases. Carbonyl hydrolases are enzymes that hydrolyze compounds comprising O═C—X bonds, wherein X is oxygen or nitrogen. They include hydrolases, e.g., lipases and peptide hydrolases, e.g., subtilisins or metalloproteases. Peptide hydrolases include α-aminoacylpeptide hydrolase, peptidylamino-acid hydrolase, acylamino hydrolase, serine carboxypeptidase, metallocarboxy-peptidase, thiol proteinase, carboxylproteinase and metalloproteinase. Serine, metallo, thiol and acid proteases are included, as well as endo and exo-proteases.

In another preferred embodiment, an initial sequence or recombined nucleic acid encodes a variant of an enzyme.

In another preferred embodiment of the invention, the initial sequence or recombined nucleic acid encodes all or a portion of a receptor. By "receptor" or grammatical equivalents herein is meant a proteinaceous molecule that has an affinity for a ligand. Examples of receptors include, but are not limited to antibodies, cell membrane receptors, complex carbohydrates and glycoproteins, enzymes, and hormone receptors.

Particularly preferred are cell-surface receptors. Cell-surface receptors appear to fall into two general classes: type 1 and type 2 receptors. Type 1 receptors have generally two identical subunits associated together, either covalently or otherwise. They are essentially preformed dimers, even in the absence of ligand. The type 1 receptors include the insulin receptor and the IGF (insulin like growth factor) receptor. The type-2 receptors, however, generally are in a monomeric form, and rely on binding of one ligand to each of two or more monomers, resulting in receptor oligomerization and receptor activation. Type-2 receptors include the growth hormone receptor, the leptin receptor, the LDL (low density lipoprotein) receptor, the GCSF (granulocyte colony stimulating factor) receptor, the interleukin receptors including IL-1, IL-2, IL-3, IL-4, IL-5, IL-6, IL-7, IL-8, IL-9, IL-11, IL-12, IL-13, IL-15, IL-17, etc., receptors, EGF (epidermal growth factor) receptor, EPO (erythropoietin) receptor, TPO (thrombopoietin) receptor, VEGF (vascular endothelial growth factor) receptor, PDGF (platelet derived growth factor; A chain and B chain) receptor, FGF (basic fibroblast growth factor) receptor, T-cell receptor, transferrin receptor, prolactin receptor, CNF (ciliary neurotrophic factor) receptor, TNF (tumor necrosis factor) receptor, Fas receptor, NGF (nerve growth factor) receptor, GM-CSF (granulocyte/macrophage colony stimulating factor) receptor, HGF (hepatocyte growth factor) receptor, LIF (leukemia inhibitory factor), TGFα/β (transforming growth factor α/β) receptor, MCP (monocyte chemoattractant protein) receptor and interferon receptors (α, β and γ). Further included are T cell receptors, MHC (major histocompatibility antigen) class I and class II receptors and receptors to the naturally occurring ligands, listed below.

In another preferred embodiment, the initial sequence or recombined nucleic acid encodes a variant of a receptor.

In one preferred embodiment of the invention, the sequence or recombined nucleic acid encodes all or a portion of a ligand. By "ligand" or grammatical equivalents herein is meant a proteinaceous molecule capable of binding to a receptor.

Ligands include, but are not limited to cytokines IL-1ra, IL-1, IL-1a, IL-1b, IL-2, IL-3, IL-4, IL-5, IL-6, IL-8, IL-10, IFN-β, INF-γ, IFN-α-2a, IFN-α-2B, TNF-α; CD40 ligand (chk), human obesity protein leptin, GCSF, BMP-7, CNF, GM-CSF, MCP-1, macrophage migration inhibitory factor, human glycosylation-inhibiting factor, human rantes, human macrophage inflammatory protein 1β, hGH, LIF, human melanoma growth stimulatory activity, neutrophil activating peptide-2, CC-chemokine MCP-3, platelet factor M2, neutrophil activating peptide 2, eotaxin, stromal cell-derived factor-1, insulin, IGF-I, IGF-II, TGF-β1, TGF-β2, TGF-β3, TGF-α, VEGF, acidic-FGF, basic-FGF, EGF, NGF, BDNF (brain derived neurotrophic factor), CNF, PDGF, HGF, GCDNF (glial cell-derived neurotrophic factor), EPO, other extracellular signaling moieties, including, but not limited to, hedgehog Sonic, hedgehog Desert, hedgehog Indian, hCG; coagulation factors including, but not limited to, TPA and Factor VIIa.

In another preferred embodiment, the sequence or recombined nucleic acid encodes a variant of a ligand.

In one preferred embodiment of the invention, the sequence or recombined nucleic acid encodes all or a portion of an antibody. The term "antibody" or grammatical equivalents, as used herein, refer to antibodies and antibody fragments that retain the ability to bind to the epitope that the intact antibody binds and include polyclonal antibodies, monoclonal antibodies, chimeric antibodies, anti-idiotype (anti-ID) antibodies. Preferably, the antibodies are monoclonal antibodies. Antibody fragments include, but are not limited to the complementarity-determining regions (CDRs), single-chain fragment variables (scfv), heavy chain variable region (VH), light chain variable region (VL).

In another preferred embodiment, the sequence or recombined nucleic acid encodes a variant of an antibody.

Information with respect to nucleic acid sequences and amino acid sequences for enzymes, receptors, ligands, and antibodies is readily available from numerous publications and several data bases, such as the one from the National Center for Biotechnology Information (NCBI).

Using the nucleic acids of the present invention which encode a variant protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant protein. The term "control sequence" or grammatical equivalents thereof, as used herein, refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize polyadenylation signals and enhancers.

In one embodiment of the invention the control sequences are generated by using the methods described herein.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading frame. However, enhancers do not have to be contiguous. Linking is accomplished by ligation at convenient restriction sites. If such sites do not exist, synthetic oligonucleotide adaptors, linkers or the recombination methods of the herein described invention, are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In one embodiment of the invention the control sequences are operably linked to a another nucleic acid by using the methods described herein.

In a preferred embodiment, when a naturally occurring secretory sequence leads to a low level of secretion of a variant protein, a replacement of the naturally occurring secretory leader sequence is desired. In this embodiment, an unrelated secretory leader sequence is operably linked to a variant protein encoding nucleic acid leading to increased protein secretion. Thus, any secretory leader sequence resulting in enhanced secretion of the variant protein, when compared to the secretion of the naturally occurring protein and its secretory sequence, is desired. Suitable secretory leader sequences that lead to the secretion of a protein are know in the art.

In another preferred embodiment, a secretory leader sequence of a naturally occurring protein or a variant protein is removed by techniques known in the art and subsequent expression results in intracellular accumulation of the recombined protein.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the STAT or CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The nucleic acids are introduced into the cells, either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The nucleic acids may stably integrate into the genome of the host cell, or may exist either transiently or stably in the cytoplasm (i.e. through the use of traditional plasmids, utilizing standard regulatory sequences, selection markers, etc.).

The proteins of the present invention are produced by culturing a host cell transformed either with an expression vector containing nucleic acid encoding the protein or with the nucleic acid encoding the protein alone, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculovirus used in insect cell expression systems is a lytic virus, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli*, *Bacillus subtilis*, SF9 cells, C129 cells, 293 cells, Neurospora, BHK, CHO, COS, *Pichia pastoris*, etc.

In a preferred embodiment, the proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen can be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable mammalian cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, COS, etc. See the ATCC cell line catalog, hereby expressly incorporated by reference.

In one embodiment, the cells may be additionally genetically engineered, that is, they contain exogenous nucleic acid other than the recombined nucleic acid of the invention.

In a preferred embodiment, the proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In $E.$ $coli$, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the expressed protein in bacteria. The signal sequence typically encodes a signal peptide comprised of hydrophobic amino acids, which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to the recombined nucleic acid, are preferred.

In a preferred embodiment, the proteins of the invention are expressed in bacteria and/or are displayed on the bacterial surface. Suitable bacterial expression and display systems are known in the art [Stahl and Uhlen, Trends Biotechnol. 15:185–92 (1997); Georgiou et al., Nat. Biotechnol. 15:29–34 (1997); Lu et al., Biotechnology 13:366–72 (1995); Jung et al., Nat. Biotechnol. 16:576–80 (1998)].

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for $Bacillus$ $subtilis$, $E.$ $coli$, $Streptococcus$ $cremoris$, and $Streptococcus$ $lividans$, among others.

The bacterial expression vectors are transformed into bacterial host cells using techniques well known in the art, such as calcium chloride treatment, electroporation, and others.

In one embodiment, proteins are produced in insect cells. Expression vectors for the transformation of insect cells, and in particular, baculovirus-based expression vectors, are well known in the art.

In another preferred embodiment, proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In a preferred embodiment, the proteins of the invention are expressed in yeast and/or are displayed on the yeast surface. Suitable yeast expression and display systems are known in the art (Boder and Wittrup, Nat. Biotechnol. 15:553–7 (1997); Cho et al., J. Immunol. Methods 220: 179–88 (1998); all of which are expressly incorporated by reference). Surface display in the ciliate *Tetrahymena thermophila* is described by Gaertig et al. Nat. Biotechnol. 17:462–465 (1999), expressly incorporated by reference.

In one embodiment, proteins are produced in viruses and/or are displayed on the surface of the viruses. Expression vectors for protein expression in viruses and for display, are well known in the art and commercially available (see review by Felici et al., Biotechnol. Annu. Rev. 1:149–83 (1995)). Examples include, but are not limited to M13 (Lowman et al., (1991) Biochemistry 30:10832–10838 (1991); Matthews and Wells, (1993) Science 260:1113–1117; Stratagene); fd (Krebber et al., (1995) FEBS Lett. 377:227–231); T7 (Novagen, Inc.); T4 (Jiang et al., Infect. Immun. 65:4770–7 (1997); lambda (Stolz et al., FEBS Lett. 440:213–7 (1998)); tomato bushy stunt virus (Joelson et al., J. Gen. Virol. 78:1213–7 (1997)); retroviruses (Buchholz et al., Nat. Biotechnol. 16:951–4 (1998)). All of the above references are expressly incorporated by reference.

In addition, the proteins of the invention may be further fused to other proteins, if desired, for example to increase expression or increase stability.

Once made, the proteins may be covalently modified. One type of covalent modification includes reacting targeted amino acid residues of a protein with an organic derivatizing agent that is capable of reacting with selected side chains or the N-or C-terminal residues of a protein. Derivatization with bifunctional agents is useful, for instance, for crosslinking a protein to a water-insoluble support matrix or surface for use in the method for purifying anti-protein antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the protein included within the scope of this invention comprises altering the native glycosylation pattern of the variant protein or of the corresponding naturally occurring protein. "Altering the native glycosylation pattern" is intended for purposes herein to mean deleting one or more carbohydrate moieties found in a protein, and/or adding one or more glycosylation sites that are not present in the respective protein.

Addition of glycosylation sites to a protein may be accomplished by altering the amino acid sequence thereof. The alteration may be made, for example, by the addition of, or substitution by, one or more serine or threonine residues to the protein (for O-linked glycosylation sites). The amino acid sequence may optionally be altered through changes at the DNA level, particularly by mutating the DNA encoding the protein at preselected bases such that codons are generated that will translate into the desired amino acids.

Another means of increasing the number of carbohydrate moieties on the protein is by chemical or enzymatic coupling of glycosides to the polypeptide. Such methods are described in the art, e.g., in WO 87/05330, published Sep. 11, 1987 and in Aplin and Wriston, CRC Crit. Rev. Biochem., pp. 259–306 (1981).

Removal of carbohydrate moieties present on the protein may be accomplished chemically or enzymatically or by mutational substitution of codons encoding for amino acid residues that serve as targets for glycosylation. Chemical deglycosylation techniques are known in the art and described, for instance, by Hakimuddin et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of a protein comprises linking the protein to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670, 417; 4,791,192 or 4,179,337.

The proteins of the present invention may also be modified in a way to form recombinant molecules comprising a protein fused to another, heterologous polypeptide or amino acid sequence. In one embodiment, such a recombinant molecule comprises a fusion of a protein with a tag polypeptide which provides an epitope to which an anti-tag antibody can selectively bind. The epitope tag is generally placed at the amino-or carboxyl-terminus of the protein. The presence of such epitope-tagged forms of a protein can be detected using an antibody against the tag polypeptide. Also, provision of the epitope tag enables the protein to be readily purified by affinity purification using an anti-tag antibody or another type of affinity matrix that binds to the epitope tag. In an alternative embodiment, the recombinant molecule may comprise a fusion of a protein with an immunoglobulin or a particular region of an immunoglobulin. For a bivalent form of the recombinant molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

In a preferred embodiment, the protein is purified or isolated after expression. The proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the protein. In some instances no purification may be necessary.

What is claimed:

1. A method of screening a nucleic acid for alterations in biological activity, said method comprising of the steps of:
   a) randomly fragmenting more than one initial nucleic acid molecule to produce a plurality of fragments:
   b) adding a terminator molecule to the 3' ends of said fragments to provide a plurality of template fragments;
   c) annealing at least one primer to said plurality of template fragments under conditions such that said primer produces a complementary strand of said template fragments; and
   d) repeating steps c) and d) to produce a pool of recombined nucleic acid molecules, wherein said recombined nucleic acid molecules are approximately the same length as the initial nucleic acid molecules; and
   e) subjecting said pool of recombined nucleic acids created by steps a) through d) to an assay which screens for said biological activity, and determining any alterations in biological activity.

2. The method of claim 1, wherein said activity is selected the group consisting of gene transcription or translation regulation, RNA processing, enzymatic activity, oxidative stability, substrate specificity, catalytic activity, thermal stability, alkaline stability, pH activity profile, resistance to proteolytic degradation, Km, kcat, Kcat/km ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation; ability to induce apoptosis, ability to be modified by phosphorylation or glycosylation, and ability to treat disease.

3. The method of claim 2, wherein said at least one sequence encodes a therapeutic peptide or an enzyme.

4. The method of claim 3, wherein said enzyme is a catalytic or hydrolytic enzyme.

* * * * *